United States Patent [19]

Lowenhaupt

[11] 4,370,201
[45] Jan. 25, 1983

[54] PROCESS FOR MAINTAINING COAL PROPORTIONS IN A COAL BLEND

[75] Inventor: Douglas E. Lowenhaupt, Plum Borough, Pa.

[73] Assignee: United States Steel Corporation, Pittsburgh, Pa.

[21] Appl. No.: 276,604

[22] Filed: Jun. 23, 1981

[51] Int. Cl.³ .................. C10B 45/00; C10B 57/04
[52] U.S. Cl. ........................................ 201/1; 201/24
[58] Field of Search ................ 201/1, 8, 24, 41, 42

[56] References Cited

U.S. PATENT DOCUMENTS

| | | | |
|---|---|---|---|
| 2,877,163 | 3/1959 | Boyer | 201/24 |
| 3,193,471 | 7/1965 | Holowaty | 201/24 |
| 3,505,520 | 4/1970 | Stewart et al. | |
| 3,849,646 | 11/1970 | McKinlay et al. | |
| 3,883,399 | 5/1975 | Nire | |
| 4,090,074 | 5/1978 | Watt et al. | |
| 4,186,054 | 1/1980 | Brayton et al. | |

FOREIGN PATENT DOCUMENTS

| | | | |
|---|---|---|---|
| 54-25884 | 2/1979 | Japan | |
| 55-6677 | 2/1980 | Japan | 201/24 |
| 2033080 | 5/1980 | United Kingdom | |

OTHER PUBLICATIONS

"Metallurgical Coke Manufacturing Method by Blending Raw Briquette" by Hiroshi Joh and Shir Ida, Sep. 1960.
"The Critical Case of Coke", Journal of Metals, Feb. 1972, pp. 32-34.
"A System of Coke Petrography", by Ralph J. Gray, Reprinted from the Illinois Mining Institute Proceedings 1976, pp. 20-47.
"Selection of Coals for Coke Making", by R. J. Gray, J. S. Goscinski and R. W. Shoenberger of U.S. Steel Corporation Research Laboratory, Oct. 1978.
"Interpreting Coal Properties for Utilization in Commercial Cokemaking" by H. N. Paulencu and P. J. Readyhough, Nov. 1974.
"Selection of Coals and Coal Mixes to Avoid Excessive Coking Pressure", by L. G. Benedict and R. R. Thompson, Mar. 1976.
"Concerning the Application of FTIR to the Study of Coal. A Critical Assessment of Band Assignments and the Application of Spectral Analysis Programs" by Paul C. Painter, Randy W. Snyder, Michael Starsinic and Michael M. Coleman of Polymer Science Section, The Pennsylvania State University and Deborah J. Kuehn and Alan Davis, The College of Earth and Mineral Sciences, The Pennsylvania State University, Jun. 8, 1981.

*Primary Examiner*—Bradley Garris
*Attorney, Agent, or Firm*—W. Gary Goodson

[57] ABSTRACT

A process is described for maintaining the proportions of each coal in a coal blend at a desired level. The process involves
(1) making a spectral analysis, preferably by infrared spectrometry, of at least one sample of the coal blend, the sample having known desired proportions of each coal,
(2) making a spectral analysis of the coal blend sample of unknown proportions of each coal,
(3) comparing the spectral analyses of steps (1) and (2), and
(4) upon noting a significant difference between the spectral analyses of steps (1) and (2), making adjustments to achieve a final coal blend having proportions of each coal closer to those of the blend of known desired proportions of each coal. The relationship of the aromatic to aliphatic groupings is preferably determined by spectral analysis of each coal sample.

This process is particularly useful on-line in the production of blast furnace coke of high strength and high stability.

19 Claims, No Drawings

PROCESS FOR MAINTAINING COAL PROPORTIONS IN A COAL BLEND

BACKGROUND OF THE INVENTION

Coal blending has been utilized for many years to obtain a coal blend of desired properties from one or more individual coals. Particularly in coke making, it is important to have certain minimum properties of the coal that goes into the coke ovens to obtain satisfactory coke strength, coke stability, and other desired properties. Coal volatility or coal rank is one property that is a particularly important property of the coal in obtaining a desired coke strength and stability.

Metallurgical coke suitable for use in the very large blast furnaces being built today must have very high coke strength as indicated by hardness and stability. A minimum hardness of about 68 and a minimum stability of about 55 are generally essential. To achieve this quality of coke requires the use of expensive high quality coking coals having a high percentage of volatiles in the coal, a high fluidity and a relatively low percentage of inert components. Due to the desire to use less expensive coals and also due to the decreasing supply of the high quality metallurgical grade coals, great effort has been expended upon ways of achieving high strength coke using lower quality coals. See "The Critical Case of Coke", Journal of Metals, February 1972, pp. 32–34, incorporated herein by reference. See also U.S. Pat. No. 4,186,054, incorporated herein by reference.

In many of the methods of using lower quality coals to make coke, one of the essential features is blending the different quality of coals. For example, by blending high, medium and/or low volatile coal, it is often possible to obtain the desired volatility at reduced cost as compared to using straight medium volatile coal. Often a particular coal, such as a low volatile coal, is itself a blend of other coals. Thus, often the final coal blend is a blend of two or more separate coal blends. For purposes of simplicity herein, when coal blends are blended they are referred to simply as "coal" or "coals".

In the coke industry, blends of coals of differing ranks are commonly used to obtain the proper coal characteristics needed to produce high quality coke. The best coke is produced using a medium volatility bituminous coal. Unfortunately, current supplies of coals of this rank are scarce, and as a result, it is common to use a blend of low and high volatility bituminous coals to yield a coal mixture with the desired intermediate characteristics. The composition of such a blend is usually checked by determining the volatile matter and verified, if necessary by a petrographic analysis, which is a time consuming procedure.

One of the problems that freqently arises is that something goes wrong with the end use for which the coal is being used. For example, the coke strength becomes unacceptably low or unnecessarily high. Poor quality coke is often produced while coal samples are being sent to the laboratory for analysis. Days or weeks of good quality production are often lost while a determination of what went wrong is made. Not infrequently it is determined that something went wrong in the blending operation which needs correcting to bring the coals back to their desired proportions in the final blend.

SUMMARY OF THE INVENTION

This invention relates to a process for maintaining the proportions of each coal in a coal blend at a desired level. The process involves (1) making a spectral analysis, preferably by infrared spectrometry, of at least one sample of the coal blend, the sample having known desired proportions of each coal, (2) making a spectral analysis of the coal blend sample of unknown proportions of each coal, (3) comparing the spectral analyses of steps (1) and (2), and (4) upon noting a significant difference between the spectral analyses of steps (1) and (2), making adjustments to achieve a final coal blend having proportions of each closer to those of the coal blend of known desired proportions of each coal. The relationship of the aromatic to aliphatic groupings is preferably determined by spectral analysis of each coal sample.

This process is particularly useful on-line in the production of blast furnace coke of high strength and high stability.

Using this invention allows one to avoid many costly mistakes in the coal blending operations. This is particularly true where the spectral analysis is carried out "on-line". Thus, in large blast-furnace coke facilities, delays of days or weeks can often be completely eliminated by being able to know immediately when something has gone wrong in the coal blending process, thereby allowing corrections to be made in the blending operations.

DESCRIPTION OF THE PREFFERRED EMBODIMENT(S)

The finely divided or powdered coal of this invention when used for coking is preferably coking coal but due to the increased strength obtained by the process of this invention the blended coals utilized may contain reduced amounts of higher quality coals such as low and medium volatility coking coal. A preferred coal is a blended coal containing a majority of coal of high volatile A rank or higher and wherein the coal contains up to 20% by weight of inert materials.

Preferably the majority of the coal used for metallurgical coke production has a volatile matter (daf) between about 18 to about 40%, a minimum free-swelling index of 4, and of such a nature as to not produce pressures in excess of about two pounds per square inch on oven walls. See R. J. Gray, "Selection of Coals for Coke Making," U.S. Steel Corporation Research Laboratory, October, 1978, incorporated herein by reference.

The finely divided coal is preferably produced by conventional grinding or pulverizing means to the desired diameter of less than about ⅛ inch, and preferably to an average particle size of less than about 60 mesh, and most preferably less than about 200 mesh. The lower size gives much improved reproducibility from the determinations.

A number of spectrographic methods of analysis can be utilized according to this invention. In general it is known that the characteristic absorptions in the range from about 3000 to about 3100 $cm^{-1}$ and from about 2870 to about 2970 $cm^{-1}$ by the infrared absorption method indicated aromatic groupings and aliphatic groupings in the coal molecules, respectively. These groupings are actually the carbon-hydrogen bond in the respective molecules. 3045 cm$^{-1}$ for the aromatic peak and 2945 cm$^{-1}$ for the aliphatic peak are preferred. The ratio of these peaks is a measure of coal rank or the volatility of the coal.

The preferred infrared spectrographic method is by diffuse reflection of finely divided coal. The Diffuse Reflectance Infrared Fouier Transform (DRIFT) method is most preferred. Time to carry out this DRIFT method according to this invention can be less than about 15 minutes. The time referred to includes the time to sample the coal blend of unknown proportions, to run a spectrum of the sample, to determine the ratio of aromatic to aliphatic groupings in the coal sample, and to compare this with the ratio previously determined for a coal blend sample with known proportions of each coal.

Other spectrographic methods include the KBr pellet method whereby potassium bromide is mixed with powdered coal and formed into a pellet. In another method fluid paraffin is mixed with powdered coal, a sandwich is prepared for IR spectroscopy whereby the transmission spectrum is measured. However, these methods do not adapt easily to on-line analysis due to long sample preparation times, difficulty in reading the results, and the like. These methods and the preferred diffuse reflectance method are discussed in Japanese Pat. No. 79-25884, issued Feb. 27, 1979 to M. Kokawa et al. and entitled, "Method of Determining Volatile Component Content in Coal".

Preferably, a calibration curve is prepared by testing two or more samples of the particular coal blend in question whereby each sample has different proportions of the component coals. These points are preferably chosen near the desired mix, in order that when a sample of unknown proportions is tested, if the aromatic to aliphatic ratio determined from spectral analysis is different than that desired, a comparison of the ratio of the unknown to the calibration curve will generally indicate the actual ratio of the coals involved. When only two coals are present in the mixture, it is relatively easy to make this determination. Any difference between the desired ratio and the actual ratio of the unknown sample will indicate possible adjustments to correct the discrepancy.

Preferably the spectral analyses are fed into a computer which carries out the comparison of spectral analyses or aromatic/aliphatic ratios derived from such analyses, and then determines whether the proportions of each coal in the sample is acceptable.

When the coal blend is used for metallurgical coke preparation, it is preferable that it has an ash level of less than about 8 percent by weight and a sulfur level of less than about 1 percent by weight.

A metallurgical coal blend is prepared from a low volatile coal from West Virginia and a high volatile coal from Pennsylvania and West Virginia. In Table I are the ratios of aromatic hydrogen/aliphatic groupings for various compositions of this coal blend. The data show that as the blend composition changes, the ratio of the aromatic/aliphatic groupings change in such a manner that blend composition can be monitored to within 2 percent.

The finely divided coals that are used for this coal blend are prepared by grinding to an average particle size of minus 200 mesh. This small particle size produces highly reproducible ratios of aromatic to aliphatic groupings when measurements are made by infrared diffuse reflectance.

Samples are prepared of the various proportions of high volatile (HV) and low volatile (LV) coal. These samples are tested by the DRIFT method, described above.

A sample containing the two coals of this example in unknown proportions are then tested by the DRIFT method, and an aromatic to aliphatic ratio is determined. A comparison of the ratio of the sample of unknown proportions to that in Table I provides a very accurate determination of the proportions of the 2 coals in the blend. If this were in a coke-making operation and these proportions were outside the acceptable range, then changes would be made in the proportions of coal going into the blend. This preferably would be done automatically, e.g. by computer.

TABLE I

Ratio of Aromatic Groupings/Aliphatic Groupings for Various Compositions of Coal Blend

| Blend Composition, % | Intensity Aromatics | Intensity Aliphatics | Aromatic/ Aliphatics | Average Ratio |
|---|---|---|---|---|
| 100 HV | 29.5 | 170.5 | 0.173 | 0.173 |
| 74.8 HV | 37.0 | 170.0 | 0.2176 | 0.2213 |
| 25.2 LV | 38.5 | 173.0 | 0.2225 | |
| | 38.5 | 172.0 | 0.2238 | |
| 73 HV | 38.0 | 172.0 | 0.2209 | 0.2272 |
| 27 LV | 41.7 | 175.5 | 0.2365 | |
| | 39.0 | 174.0 | 0.2241 | |
| 70 HV | 39.0 | 171.0 | 0.2280 | 0.2360 |
| 30 LV | 40.8 | 170.5 | 0.2393 | |
| | 41.3 | 171.5 | 0.2408 | |
| 68 HV | 40.0 | 171.0 | 0.2339 | 0.2370 |
| 32 LV | 40.5 | 173.25 | 0.2338 | |
| | 41.5 | 170.5 | 0.2434 | |
| 65.3 HV | 41.5 | 173.5 | 0.2392 | 0.2435 |
| 34.7 LV | 41.0 | 171.5 | 0.2391 | |
| | 43.0 | 170.5 | 0.2522 | |
| 43 HV | 55.0 | 173.0 | 0.3179 | 0.3183 |
| 57 LV | 56.0 | 174.5 | 0.3209 | |
| | 55.0 | 174.0 | 0.3161 | |
| 21.9 HV | 69.5 | 170.5 | 0.4076 | 0.4086 |
| 78.1 LV | 72.5 | 176.0 | 0.4119 | |
| | 70.5 | 173.5 | 0.4063 | |
| 100 LV | 87.5 | 178.0 | 0.4916 | 0.4905 |
| | 84.4 | 172.5 | 0.4893 | |

I claim:

1. A process for maintaining the proportions of each coal in a finely divided coal blend at a desired level, which comprises:
   (1) making a spectral analysis of at least one sample of said coal blend, said sample having known desired proportions of each said coal,
   (2) making a spectral analysis of a coal blend sample of unknown proportions of each said coal,
   (3) comparing the spectral analyses of steps (1) and (2), and
   (4) upon noting a significant difference between the spectral analyses of steps (1) and (2), making adjustments to achieve a final coal blend having proportions of each said coal closer to those of said coal blend of known desired proportions of each said coal.

2. Process as in claim 1 wherein the relationship of the aromatic to aliphatic groupings is determined by spectral analysis of each said coal sample.

3. Process as in claim 2 wherein the aromatic to aliphatic ratio of each said coal sample is determined by infrared spectrometry of powdered coal.

4. Process as in claim 1 wherein said process is carried out in less than about 15 minutes.

5. A process for producing blast furnace coke by maintaining the proportions of each coal in a finely divided coal blend at a desired level which comprises
   (1) determining by spectral analysis the aromatic to aliphatic ratio of each of one or more samples of said coal blend, said samples each having different known desired proportions of each said coal,
   (2) determining on-line by spectral analysis the aromatic to aliphatic ratio of a sample of unknown proportions of said coal blend, which coal blend is in transit to coke ovens for carbonization,
   (3) comparing the measurements of steps (1) and (2) to thereby determine the proportions of each coal in said sample of unknown proportions,
   (4) adjusting the proportions of each coal in said coal blend in response to the comparison of step (3) to achieve a blend closer to that having the desired proportions of each coal, and
   (5) carbonizing said coal blend to thereby produce blast furnace coke of high strength and high stability.

6. Process as in claim 5 wherein said blast furnace coke has a minimum hardness of about 68 and a minimum stability of about 55.

7. Process as in claim 6 wherein the spectral analyses are fed into a computer which carries out the comparison of step (3) and then determines whether the proportions of each coal in the sample is acceptable.

8. Process as in claim 7 wherein a calibration curve is obtained from the spectral analyses of two or more samples of said coal blend, each having different known desired proportions of each coal.

9. Process as in claim 8 wherein adjustments are made in the coal blending operations to change the proportion of the coals in said coal blend in response to the determination of the proportion of each coal in said sample of coal blend of unknown proportions as compared to the desired proportion of each coal in said coal blend.

10. Process as in claim 9 wherein all of the steps are performed automatically and as an integral part of the process.

11. Process as in claim 10 wherein the steps are performed by means of a computer.

12. Process as in claim 9 wherein at least one of the steps is performed automatically.

13. Process as in claim 5 wherein the spectral analysis is infrared spectrometry.

14. Process as in claim 13 wherein the infrared spectrometry is conducted by diffuse reflectance of a powdered coal sample.

15. Process as in claim 14 wherein the aromatic to aliphatic ratio is attained by dividing the intensity of the aromatic peak by that of the aliphatic peak measured on the Diffuse Reflectance Infrared Fourier Transform (DRIFT) spectrum of the coal sample.

16. Process as in claim 15 wherein the aromatic peak is located at about 3045 $cm^{-1}$ on the spectrum and wherein the aliphatic peak is located at about 2945 $cm^{-1}$ on the spectrum.

17. Process as in claim 15 wherein the powdered coal has an average particle size less than about 60 mesh.

18. Process as in claim 15 wherein the powdered coal has an average particle size of less than about 200 mesh.

19. Process as in claim 5 wherein steps (2) and (3) are carred out in less than about 15 minutes.

* * * * *